US00PP30084P2

(12) United States Plant Patent
Hansen

(10) Patent No.: US PP30,084 P2
(45) Date of Patent: Jan. 8, 2019

(54) ***SALVIA* PLANT NAMED 'BUMBLEBLUE'**

(50) Latin Name: ***Salvia nemorosa* (Linnaeus)**
Varietal Denomination: Bumbleblue

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/731,914

(22) Filed: Aug. 22, 2017

(51) Int. Cl.
*A01H 5/02* (2018.01)

(52) U.S. Cl.
USPC ..... Plt./475
CPC ..... *A01H 5/02* (2013.01)

(58) Field of Classification Search
USPC ..... Plt./475
See application file for complete search history.

*Primary Examiner* — Anne Marie Grunberg

(57) ABSTRACT

The new and distinct cultivar of perennial *Salvia* plant named 'Bumbleblue' characterized by its small strong violet-colored flowers densely arranged in verticils, with compact rounded habit and stiff, upright, heavily-branched stems and strong vigorous growth rate and small gray-green foliage. *Salvia* 'Bumbleblue' is especially useful for landscaping and containerized ornamentals by itself or in combination with other plants.

1 Drawing Sheet

Botanical denomination: *Salvia nemorosa* (Linnaeus).
Cultivar designation: 'Bumbleblue'.

BACKGROUND OF THE INVENTION

The present invention relates to a new and distinct cultivar of ornamental sage plant hereinafter referred to by the cultivar name *Salvia* 'Bumbleblue' or as the new plant. The new plant was hybridized on May 12, 2012 at a wholesale perennial nursery in Zeeland, Mich., USA. The new plant was the result of a cross between *Salvia* 'Crystal Blue' U.S. Plant Pat. No. 26,344 and 'New Dimension Blue' (not patented). The seeds from the cross were harvested on Aug. 7, 2012 and the single specific seedling that developed into the new *Salvia* was assigned the breeder code 12-60-2 through the evaluation process. The new plant was first selected for further evaluation in the summer of 2013 and selected for final evaluation in the summer of 2015. The first asexual propagation was performed in the summer of 2014 by shoot tip cuttings at the same nursery in Zeeland, Mich. 'Bumbleblue' has proven that it is stable and reliably produces true to type plants in successive generations of asexual propagation.

No plants of *Salvia* 'Bumbleblue' have been sold or disclosed in this country, or anywhere in the world, by this or any name, more than one year prior to the filing of this application, with the exception of that which was sold or disclosed either directly or indirectly from the inventor and within one year from the filing of this application.

SUMMARY OF THE INVENTION

Plants of *Salvia* 'Bumbleblue' have not been observed under all possible environmental conditions. The phenotype may vary somewhat with variations in environment such as temperature, nutrition and light intensity without, however, any variance in genotype.

*Salvia* 'Bumbleblue' can be most closely compared to 'Blue Marvel' U.S. Plant Pat. No. 27,018. The new plant is slightly taller in habit, the foliage is smaller and the flower is slightly different colored. Compared with the female parent *Salvia* 'Crystal Blue' U.S. Plant Pat. No. 26,344 the new plant is much smaller in habit and the flower is a much stronger violet. The new plant can also be compared to 'Haeumanarc' U.S. Plant Pat. No. 13,322 which is much shorter in habit with slightly different flower color. Compared with *Salvia* 'May Night' (not patented) and *Salvia* 'Blue Hill' (not patented) the new plant is shorter with a flower color of strong violet. *Salvia* 'Sensation Sky Blue' (not patented) differs from the new plant in being shorter, lighter purplish blue in flower color.

Compared with the male parent, 'New Dimension Blue' the new plant has a smaller and more compact in habit and the flower color is similar.

The following characteristics in combination distinguish *Saliva* 'Bumbleblue' as a new and distinct cultivar:

1. Small, strong violet-colored flowers densely arranged in tight verticils;
2. Compact rounded habit and stiff, upright, heavily-branched stems;
3. Strong, vigorous and winter-hardy;
4. Small, rugose, gray-green foliage.

BRIEF DESCRIPTION OF THE DRAWINGS

The photographs of the new plant demonstrate the unique traits and the overall appearance of *Salvia* 'Bumbleblue'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed. No stem pinching or plant growth regulators have been used.

DETAILED BOTANICAL DESCRIPTION

Figure 1:
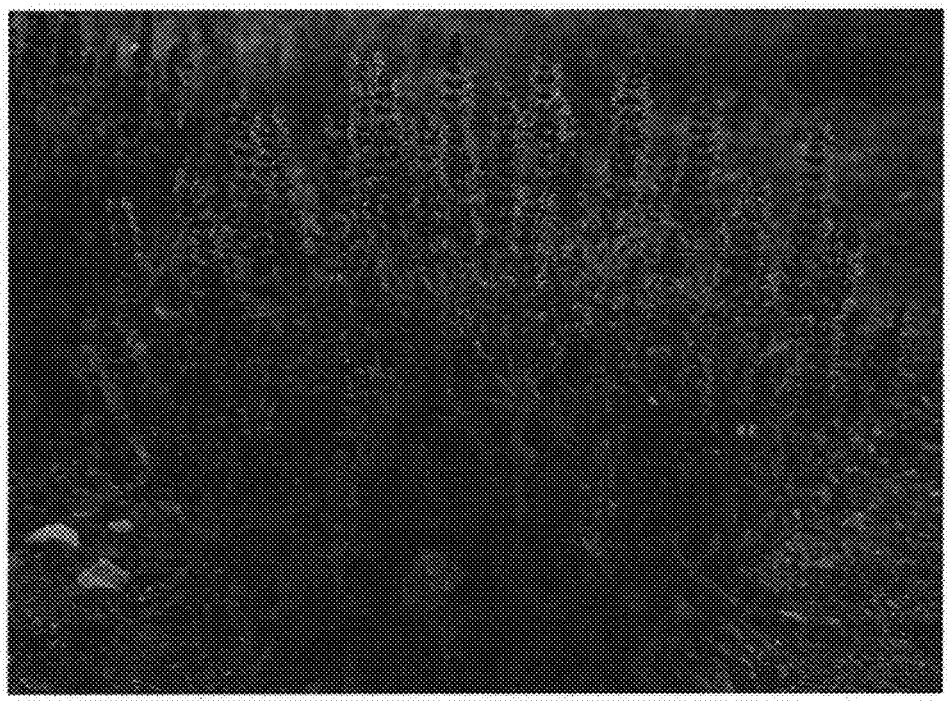
FIG. 1 shows the plant habit in full flower in a landscape.
Figure 2:
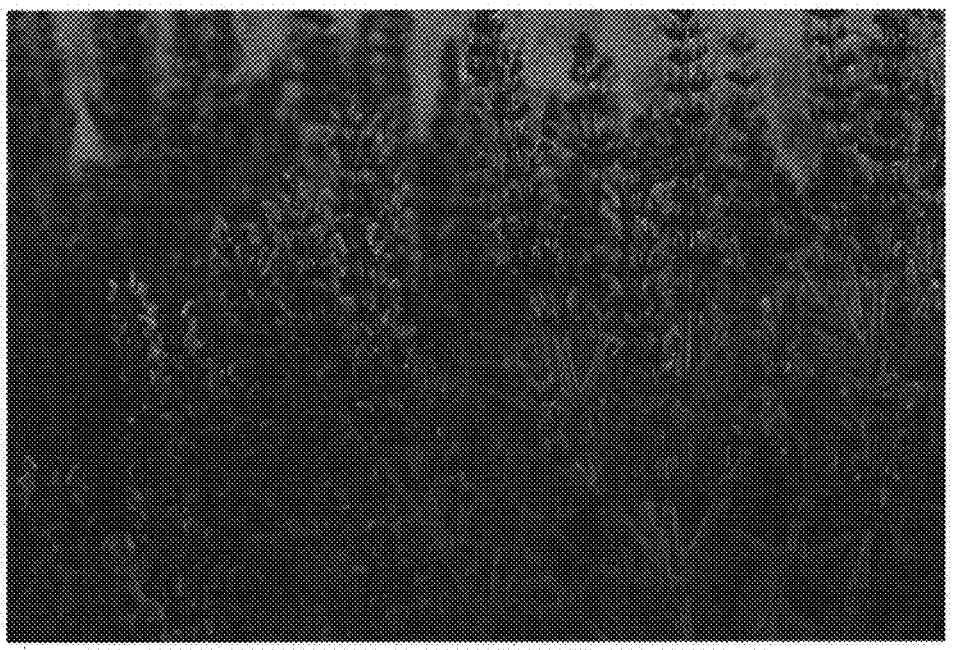
FIG. 2 shows a close-up of the flower scape with the buds and strong violet petal color.

The following descriptions and color references except where common dictionary terms are used are based on the 2015 edition of The Royal Horticultural Society Colour Chart. *Salvia* 'Bumbleblue' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing both in a greenhouse with minimal shading and in an outdoor full-sun trial garden at a wholesale perennial nursery in Zeeland, Mich. Plants were given supplemental water and fertilizer but no plant growth regulators were used.

Botanical classification: *Salvia nemorosa* (Linnaeus);

Parentage: Female or seed parent is *Salvia* 'Crystal Blue'; the male or pollen parent was believed to be 'New Dimension Blue';

Plant habit: Winter-hardy herbaceous perennial; multi-stemmed, with basal and cauline foliage, and flowers in several tightly arranged verticils on heavily-branched upright racemes displayed above foliage; in flower with panicles about 20 cm tall and about 15 cm wide at the fullest point about 15 cm above soil; foliage extends about two-thirds of the way up the stems;

Propagation: By herbaceous tip cuttings; time to produce a rooted stems about two weeks;

Growth rate: Rapid, vigorous, finishing in from a 25 mm plug to flower in one-gallon pot in about 10 to 12 weeks, and flowering in a one-gallon pot from a dormant bare-root one-year-old plant in about 6 to 8 weeks;

Root description: Fine, well-branched; color dependent on age and soil type, from cream to dark tan in color;

Foliage: Opposite, simple, rugose, ovate; margin crenate; glabrous abaxial and adaxial; acute apex and base cordate to rounded; leaf blades about 4.5 cm long and 2.4 cm across, decreasing in size distally; average about 3.8 cm long and 2.0 cm across;

Foliage fragrance: Faint sage fragrance;

Foliage color: Mature adaxial surface nearest RHS 137A, mature abaxial surface nearest RHS 146B; expanding adaxial nearest RHS 137B, expanding abaxial nearest RHS 137C;

Venation: Reticulate; impressed on adaxial side and ridged on abaxial side; puberulent abaxial and glabrous adaxial midrib and secondary veins;

Vein color: Mature adaxial midrib nearest RHS 145D, main and secondary veins nearest RHS 137A; mature abaxial midrib and main veins nearest RHS 145D, secondary veins becoming nearest RHS 147C toward leaf margin; expanding adaxial midrib nearest RHS 145D and main and secondary veins blend between RHS N148D and RHS 145D; expanding abaxial midrib, main and secondary veins nearest RHS 147C;

Petiole: Concavo-convex, pubescent along margin and puberulent abaxial and adaxial surfaces; to about 1.5 cm long and 2.0 mm wide at base, average 1.2 cm long and 2.0 mm wide at base;

Petiole color: Adaxial center nearest RHS 145D and margins nearest RHS 138A; abaxial center nearest RHS 145C and margins nearest RHS 138A;

Stems: Quadrangular; pubescent, to 16.0 cm long before flowers and 3.5 mm across at base;

Stem color: Nearest RHS 138A with stippling of nearest RHS N186A in older stems;

Nodes: Eight before flowering verticils; average internode length 2.1 cm; color same as stem;

Flower: Perfect; bilabiate; zygomorphic; verticillate with flowering generally beginning at lower verticils and advancing up the scape, not all flowers at same verticil opening at the same time; with lower lip projected downward almost vertically and parallel to stem and hood petal upwardly at about 45 degree angle above horizontal; self-cleaning, petals not persistent; flowering beginning late spring for about four weeks and repeating if initial scapes removed;

Flower longevity: About four days on the plant or as cut flower;

Flower fragrance: None detected;

Flower buds one to two days prior to anthesis: Shape is falcate, with rounded apex; pubescent; about 8.0 mm long, 2.5 mm tall and 1.5 mm wide;

Flower bud color: Petals nearest RHS 93B and RHS 91C; calyx nearest RHS 144D, calyx veins nearest RHS 144D;

Flowers: About 1.3 cm long from base of calyx to tip of exserted style, 9.0 mm tall and 6.0 mm wide; clustered at verticils with about six flowers per verticil;

Petals: Bilabiate corolla; upper hood upwardly to outwardly and lower labium drooping producing an angle between the two petals of about 90 degrees;

Hood (upper) petal: Slightly arcuate to falcate in distal half; conduplicate vertically, with emarginate apex and basal 6.0 mm fused into tube 2.0 mm diameter at base and 3.0 mm diameter at petal separation; puberulent outside, glabrous inside; 12.0 mm long, 3.0 mm tall and 1.0 mm across;

Labium (lower) petal: Consisting of three apical lobes, two upwardly projecting lateral lobes about 2.0 mm long and 1.0 mm wide at base with rounded apex, one central lobe about 3.5 mm long 6.0 mm wide with rounded emarginate apex; distal portion of lower labium slightly concaved upwards; distally glabrous adaxial, microscopically puberulent abaxial with small tuft about 2.0 mm from base of adaxial tube puberulent; about 10.0 mm long, 6.0 mm wide at the widest portion and 3.0 mm tall;

Petal color: Abaxial and adaxial upper hood nearest RHS N88B; and adaxial lower labium nearest RHS N88B, abaxial lower labium center nearest RHS N88D and nearest RHS N88B at perimeter; tube base nearest RHS N155D;

Androecium: Two, fused with labium, contained within hood petal;

*Filament*.—Glabrous, about 2.0 mm long and about 0.3 mm diameter; adnate about 4.0 mm from base of labium petal; curved around inside of hood petal; color nearest RHS 91D.

*Anther*.—Glabrous, oblong, about 1.0 mm long and about 0.5 mm diameter; longitudinal, dorsifixed; color blend between RHS 176B and RHS N187B.

*Pollen*.—Globose, less than 0.5 mm circumference; color nearest RHS 8C.

Gynoecium: One, curved around inside of hood petal; total about 1.3 cm long;

*Style*.—About 12.0 mm long and less than 0.5 mm diameter; color nearest RHS NN155D at base, darkening distally to between RHS 86B and RHS 86A before stigma split;

*Stigma*.—Split in two and curved in the terminal 2.0 mm; apex pointed; color nearest RHS 86A.

*Ovary*.—Superior; color nearest RHS 145A.

*Fruit*.—One to four nutlets per flower; ellipsoidal to spherical; about 1.0 mm diameter; color nearest RHS 202A.

Calyx: Five sepals, three upper and two lower, campanulate, apex acute; fused in basal 3.0 mm; persistent; tube about 5.0 mm long and 2.0 mm wide; lower cleft about 2.0 mm deep between lobes and upper and lower set; upper set of three fused to closer than 0.5 mm of apex;

Calyx color: Abaxial between RHS 138A and RHS 138B with veins lightly blushed with nearest RHS N187A; adaxial base nearest RHS 145D, distally nearest RHS 138A with darker veins of nearest RHS 138A;

Bracts: Each verticil subtended by two opposite bracts; apex acuminate, base truncate, shape nearly cordate; margin entire, ciliolate, and glabrous above and below; bract size up to 8.0 mm long and 9.0 mm wide, decreasing distally; color of both surfaces nearest RHS 137A with center and base veins nearest RHS 145D;

Peduncles: Quadrangular in cross section, strong; mostly upright; main peduncle up to 14 cm tall and 2.5 mm across; finely puberulent; heavily branched with opposite branches at about 45 degrees above horizontal at the three nodes below flowers; branches to about 11.5 cm long and 2.0 mm across; average space between verticils about 0.6 cm;

Peduncle color: Nearest RHS 138A in upper and lower regions;

Pedicels: Cylindrical, about 1.0 mm long and 0.5 mm diameter; puberulent; horizontal to about 30 degrees above horizontal;

Pedicel color: Blend between RHS N187B and RHS 187B;

Disease and pest resistance: Plants of *Salvia* 'Bumbleblue' perform best with adequate moisture and good drainage but are fairly drought tolerant once established; hardy from USDA zone 3 to 8; resistance to diseases and pests beyond that common to *Salvia* has not been noted;

It is claimed:

1. The new and distinct perennial *Salvia* plant named 'Bumbleblue' as herein described and illustrated useful for landscaping as a specimen plant, en masse or as a cut flower.

* * * * *